(12) United States Patent
Li et al.

(10) Patent No.: US 6,465,687 B1
(45) Date of Patent: Oct. 15, 2002

(54) THYROID RECEPTOR LIGANDS AND METHOD

(75) Inventors: Yi-Lin Li, Huddinge (SE); Ye Liu, Tullinge (SE); Asa Hedfors, Hiddinge (SE); Johan Malm, Skogas (SE); Charlotta Mellin, Tullinge (SE); Minsheng Zhang, Warren, NJ (US)

(73) Assignee: Karo Bio AB, Huddinge (SE)

( * ) Notice: Subject to any disclaimer, the term of this patent is extended or adjusted under 35 U.S.C. 154(b) by 0 days.

(21) Appl. No.: 09/445,888

(22) PCT Filed: Jun. 26, 1998

(86) PCT No.: PCT/EP98/04039
§ 371 (c)(1),
(2), (4) Date: Mar. 20, 2000

(87) PCT Pub. No.: WO99/00353
PCT Pub. Date: Jan. 7, 1999

(30) Foreign Application Priority Data

Jun. 27, 1997 (GB) ............................................. 9713739

(51) Int. Cl.[7] ............................................. C07C 59/00
(52) U.S. Cl. ................... 562/465; 562/474; 562/8; 562/23; 560/55; 560/65; 558/70; 558/177; 558/202; 558/207; 558/388; 558/402; 568/635; 568/636; 568/639
(58) Field of Search .................. 562/465, 478, 562/474, 8, 23; 560/55, 65; 558/70, 177, 202, 207, 388, 402; 568/635, 636, 639; 514/570, 532, 646, 721

(56) References Cited

FOREIGN PATENT DOCUMENTS

| DE | 1 072 998 | 1/1960 |
| DE | 1 078 582 | 3/1960 |

OTHER PUBLICATIONS

Chem Abst. 125:11690 (1996).*
Yokoyama et al. "Synthesis and Structure—Activity Relationships of Oxamic Acid and Acetic Acid Derivatives Related to L-Thyronine", *J. Med. Chem.*, 38, pp. 695–707 (1995).

Blank, et al., "Thyrominetics. II. The Synthesis and Hypocholesteremic Activity of Some β-Diethylaminoethyl Esters of Iodinated Thyroalkanoic Acids", *Thyromimetic. II,* Sep. 1963, pp. 560–563.

Mazzochi, et al., "Synthesis of Diphenyl Ester Models of Thyroid Hormones. Diphenyl Ethers Linked to the 3–Oxo–2–azabicyclo[2.2.1]heptane Ring System as Substrates for Conformational Analysis", *J. Org. Chem.,* 46, 1981, pp. 4530–4536.

Buess, et al., "The Synthesis of Thyromimetic Substances and Potential Inhibitors of Thyroxine", *Analogs of Thyroxine,* Jul. 1965, pp. 469–474.

* cited by examiner

*Primary Examiner*—Paul J. Killos
(74) *Attorney, Agent, or Firm*—Todd E. Garabedian; Wiggin & Dana

(57) ABSTRACT

Novel thyroid receptor ligands are provided which have the general formula (I)

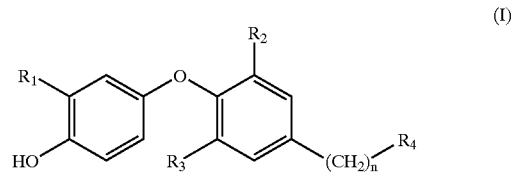

where $R_1$ is alkyl of 1 to 4 carbons or cycloalkyl of 3 to 7 carbons; $R_2$ and $R_3$ are the same or different and are hydrogen, halogen, alkyl of 1 to 3 carbons or cycloalkyl of 3 to 5 carbons, at least one of $R_2$ and $R_3$ being other than hydrogen; n is an integer from 0 to 4; $R_4$ is an aliphatic hydrocarbon, an aromatic hydrocarbon, carboxylic acid ester thereof, alkenyl carboxylic acid or ester thereof, hydroxy, halogen, cyano, or a phosphonic acid or an ester thereof, or a pharmaceutically acceptable salt thereof. A method for treating diseases associated with metabolism dysfunction or which are dependent on the expression of a T3 regulated gene, such as obesity, hypercholesterolemia, osteoporosis, hypothyroidism, and goiter, is also provided.

20 Claims, No Drawings

THYROID RECEPTOR LIGANDS AND METHOD

BACKGROUND OF THE INVENTION

1. Field of the Invention

This invention relates to novel compounds which are thyroid receptor ligands, and are preferably selective for the thyroid hormone receptor β, to methods of preparing such compounds and to methods for using such compounds such as in the regulation of metabolism.

2. Brief Description of the Prior Art

While the extensive role of thyroid hormones in regulating metabolism in humans is well recognized, the discovery and development of new specific drugs for improving the treatment of hyperthyroidism and hypothyroidism has been slow. This has also limited the development of thyroid hormone agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, the metabolic rate, body temperature, and mood, and influence serum low density lipoprotein (LDL) levels. Thus, in hypothyroidism there are weight gain, high levels of LDL cholesterol, and depression. In excess with hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or T4) and triiodothyronine (3,5,3'-triiodo-L-thyronine, or T3). However, the rapidity with which replacement therapy can be given and in some circumstances, particularly in older individuals, even replacement therapy, is limited by certain of the deleterious effects of thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Development of specific and selective thyroid hormone receptor agonists could lead to specific therapies for these common disorders while avoiding the cardiovascular and other toxicities of native thyroid hormones. Tissue-selective thyroid hormone agonist may be obtained by selective tissue uptake or extrusion, topical or local delivery, targeting to cells through other ligands attached to the agonist and targeting receptor subtypes. Thyroid hormone receptor agonists that interact selectively with the β-form of the thyroid hormone receptor offers an especially attractive method for avoiding cardio-toxicity.

Thyroid hormone receptors (TRs) are, like other nuclear receptors, single polypeptide chains. The various receptor forms appear to be products of two different genes α and β. Further isoform differences are due to the fact that differential RNA processing results in at least two isoforms from each gene. The TRα1, TRβ1 and TRβ2 isoforms bind thyroid hormone and act as ligand-regulated transcription factors. In adults, the TRβ1 isoform is the most prevalent form in most tissues, especially in the liver and muscle. The TRα2 isoform is prevalent in the pituitary and other parts of the central nervous system, does not bind thyroid hormones, and acts in many contexts as a transcriptional repressor. The TRα1 isoform is also widely distributed, although its levels are generally lower than those of the TRβ1 isoform. This isoform may be especially important for development. Whereas many mutations in the TRβ gene have been found and lead to the syndrome of generalized resistance to thyroid hormone, mutations leading to impaired TRα function have not been found.

A growing body of data suggest that many or most effects of thyroid hormones on the heart, and in particular on the heart rate and rhythm, are mediated through the α-form of the TRα1 isoform, whereas most actions of the hormone such as on the liver, muscle and other tissues are mediated more through the β-forms of the receptor. Thus, a TRβ-selective agonist might not elicit the rhythm and rate influences of the hormones but would elicit many other actions of the hormones. It is believed that the α-form of the receptor is the major drive to heart rate for the following reasons:

1) tachycardia is very common in the syndrome of generalized resistance to thyroid hormone in which there are defective TRβ-forms, and high circulating levels of T4 and T3;
2) there was a tachycardia in the only described patient with a double deletion of the TRβ gene (Takeda et al, J. Clin. Endrocrinol. & Metab. 1992, Vol. 74, p. 49);
3) a double knockout TRα gene (but not β-gene) in the mouse has a slower pulse than control mice; and,
4) western blot analysis of human myocardial TR's show presence of the TRα1, TRα2 and TRβ2 proteins, but not TRβ1.

If these indications are correct, then a TRβ-selective agonist could be used to mimic a number of thyroid hormone actions, while having a lesser effect on the heart. Such a compound may be used for: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and, (6) osteoporosis in combination with a bone resorption inhibitor.

SUMMARY OF THE INVENTION

In accordance with the present invention, compounds are provided which are thyroid receptor ligands, and have the general formula I:

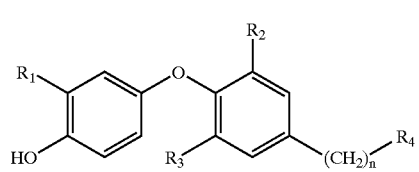

in which:
  $R_1$ is alkyl of 1 to 6 carbons or cycloalkyl of 3 to 7 carbons;
  $R_2$ and $R_3$ are the same or different and are hydrogen, halogen, alkyl of 1 to 4 carbons or cycloalkyl of 3 to 5 carbons, at least one of $R_2$ and $R_3$ being other than hydrogen;

n is an integer from 0 to 4;

R$_4$ is an aliphatic hydrocarbon, an aromatic hydrocarbon, carboxylic acid or ester thereof, alkenyl carboxylic acid or ester thereof, hydroxy, halogen, cyano, or a phosphonic acid or ester thereof, or a pharmaceutically acceptable salt thereof, and all stereoisomers thereof.

In addition, in accordance with the present invention, a method for preventing, inhibiting or treating a disease associated with metabolism dysfunction or which is dependent upon the expression of a T3 regulated gene is provided, wherein a compound of formula I is administered in a therapeutically effective amount. The compound of formula I is preferably an agonist that is preferably selective for the thyroid hormone receptor-beta. Examples of such diseases associated with metabolism dysfunction or are dependent upon the expression of a T3 regulated gene are set out hereinafter and include obesity, hypercholesterolemia, atherosclerosis, cardiac arrhythmias, depression, osteoporosis, hypothyroidism, goiter, thyroid cancer as well as glaucoma and congestive heart failure.

DETAILED DESCRIPTION OF THE INVENTION

The following definitions apply to the terms as used throughout this specification, unless otherwise limited in specific instances.

The term "thyroid receptor ligand" as used herein is intended to cover any moiety which binds to a thyroid receptor. The ligand may act as an agonist, an antagonist, a partial agonist or a partial antagonist.

The term "aliphatic hydrocarbon(s) as used herein refers to acyclic straight or branched chain groups which include alkyl, alkenyl or alkynyl groups.

The term "aromatic hydrocarbon(s) as used herein refers to groups including aryl groups as defined herein.

Unless otherwise indicated, the term "lower alkyl", "alkyl" or "alk" as employed herein alone or as part of another group includes both straight and branched chain hydrocarbons, containing 1 to 12 cartons (in the case of alkyl or alk), in the normal chain, preperably 1 to 4 carbons, such as methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may be optionally substituted through available carbon atoms with 1, 2, or 3 groups selected from hydrogen, halo, alkyl, haloalkyl, alkoxy, haloalkoxy, alkenyl, trifluoromethyl, trifluoromethoxy, alkynyl, hydroxy, nitro or cyano.

Unless otherwise indicated, the term "lower alkenyl" or "alkenyl" as used herein by itself or as part of another group refers to straight or branched chain radicals of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like.

Unless otherwise indicated, the term "lower alkynyl" or "alkynyl" as used herein by itself or as part of another group refers to straight or branched chain radicals of 2 to 12 carbons, preferably 2 to 8 carbons, in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like.

Unless otherwise indicated, the term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 7 carbons, preferably 3 to 5 carbons, forming the ring, which includes cyclopropyl, cyclobutyl, cyclopentyl, cyclohexyl, cycloheptyl, cyclopentenyl and cyclohexenyl.

The term "halogen" or "halo" as used herein alone or as part of another group refers to chlorine, bromine, fluorine, and iodine as well as CF$_3$, with chlorine or bromine being preferred.

The term "phosphonic acid" refers to a phosphorus containing a group of the structure

wherein R$_5$ is H or lower alkyl.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C$_1$–C$_4$)-alkyl- or aryl-sulfonic acids which are unsubstituted or substituted, for example by halogen, for example methyl- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, sucn as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I which include a basic gorup include monohydrochloride, hydrogensulfate, methanesulfonate, phosphate or nitrate.

Preferred salts of the compounds of formula I which include an acid group include sodium, potassium and magnesium salts and pharmaceutically acceptable organic amines.

Preferred are compounds of the invention of formula I wherein $R_1$ is isopropyl;

$R_2$ and $R_3$ are independently halogen such as bromo or chloro; or $R_2$ and $R_3$ are each methyl or one is methyl and the other is ethyl;

or one of $R_2$ and $R_3$ is halogen such as bromo or chloro, and the other is alkyl such as methyl, or hydrogen;

n is 0, 1 or 2; and $R_4$ is carboxylic acid (COOH) or esters thereof, alkenyl carboxylic acid or esters thereof, OH, CN, halogen such as iodo, phosphonic acids or esters thereof such as

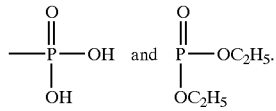

Preferred compounds of the invention have the structures

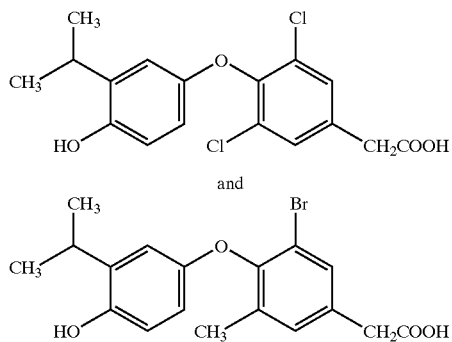

The compounds of formula I may be prepared by the exemplary processes described in the following reaction schemes. Exemplary reagents and procedures for these reactions appear hereinafter and in the working Examples.

Compounds of formula I of the invention can be prepared using the sequence of steps outlined in Schemes 1 to 5 set out below.

In Scheme 1, an anisole-derived iodonium salt 2 and copper bronze in an inert solvent such as dichloromethane are mixed at room temperature. A mixture of the appropriate phenol ester 1 and a base such as triethylamine in an inert solvent such as dichloromethane was added to the mixture, generally using 2 molar equivalents each of the phenol and base, and 3 molar equivalents of iodonium salt 2. After stirring overnight at room temperature, the reacted mixture is purified via chromatography on silica gel, to give biaryl ether products 3. Other methods exist in the literature for the synthesis of diaryl ethers, for example, two references directly apply to the synthesis of thyroid hormone analogs: D. A. Evans et al., Tet. Letters, volume 39, 2937–2940 (1998) and G. M. Salamonczyk et al., Tet. Letters, volume 38, 6965–6968 (1997). The carboxylic acid ester is removed with a mixture of aqueous sodium hydroxide and methanol. Acidification of the completed reaction mixture is followed by standard work-up and crystallization or chromatography. The methyl ether function is removed by treatment of the free acid product of the previous procedure with 4–6 molar equivalents of a strong acid such as boron tribromide at 0° C. in an inert solvent such as dichloromethane. The reacted mixture gives after standard work-up and purification, the end product 4 (Examples 1, 3, 4, 5 and 11). Other combinations of protecting groups for the carboxylic acid present in 1 and phenolic hydroxyl in iodonium salt 2 can be employed, and their usage is known to those skilled in the art (references describing protecting group strategy include, for example, "Protecting Groups in Organic Chemistry", J. F. W. McOmie, Plenum Press, London, New York, 1973, and "Protective Groups in Organic Synthesis", T. W. Greene, Wiley, New York, 1984).

Examples of compounds of formula I in which $R_4$=OH can be prepared by further chemistry are depicted in Scheme 1. The intermediate ester product 3 can reduced by treatment with an appropriate reducing agent such as diisobutyl aluminium hydride in an inert solvent such as THF at 0° C. If $R_2$ and $R_3$ are alkyl, then lithium aluminum hydride may be employed without the risk of reducing away halogen substituents at those positions. Standard work-up and purification yields the desired alcohol product 5. Other reducing agents may be employed and are known to those skilled in the art. Removal of the phenolic protecting group as described above affords the final product alcohol 6, which are compounds of formula I in which $R_4$=OH (Example 6).

Intermediate 5 in Scheme 1 may be converted to compounds of formula I in which $R_4$=halogen by any one of a number of sequences well known to those skilled in the art. For example, 2 molar quivalents of sodium iodide can be added to a mixture of alcohol 5, $P_2O_5$ and $H_3PO_4$, and heated at 120° C. for 15 minutes, to give the intermediate iodide 7. Removal of the phenolic protecting group gives final product 8, a compound of formula I in which $R_4$=iodide (Examples 2 and 7) after conventional work-up and purification. Numerous other methodologies for conversion of simple hydroxyl groups to the corresponding alkyl halide are well known to those skilled in the art.

Various extended carboxylic acid compounds of formula I ($R_4$=COOH) can be obtained from intermediate 7 in Scheme 1. For example, the anion of ethyl malonate can be stirred with alkyl iodide 7 overnight at reflux in a polar solvent such as t-butanol or dimethylformamide, employing a molar ratio of the anion, compared with the iodide, within the range of 2–3 to 1. After hydrolysis of the alkylated diester product of this reaction, the corresponding monoacid is obtained by heating the diacid to temperatures around 180° C. Removal of the methyl ether protecting group as described above yields the desired product 9 in which $R_4$=COOH (Example 8).

Compounds of formula I in which $R_4$=CN can be obtained by reacting intermediate 7 in Scheme 1 with sodium cyanide in a polar solvent or solvent mixture such as water:ethanol (1:3). The reaction may be stirred at reflux and the amount of sodium cyanide employed may be at least 5 times molar excess relative to the iodide 7 in order to drive the reaction to completion. Work-up and purification of the resulting product by standard means affords the desired nitrile product. Removal of the methyl ether group by methods described above yields the final product 10 in which $R_4$=CN (Example 9). The nitrile final products may also be converted to the corresponding carboxylic acids by standard hydrolytic procedures such as heating to around 100° C. in a mixture comprised of equal volumes of acetic acid, sulfuric acid and water. Standard work-up and purification affords the corresponding carboxylic acid product (Example 10).

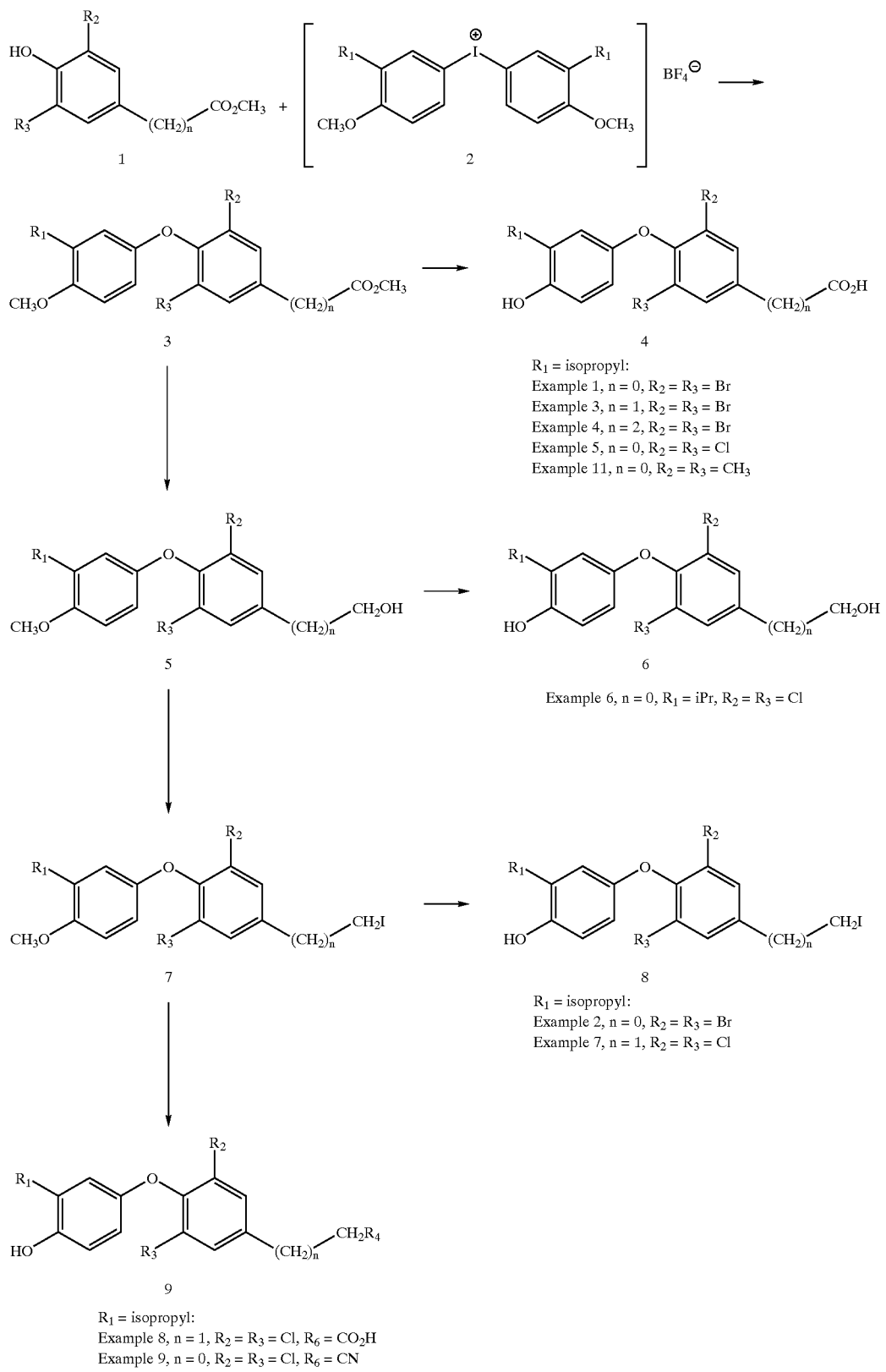

The procedures described in Scheme 2 further exemplify methods for the synthesis of compounds of formula I. For example, the unprotected phenol, carboxylic acid intermediate 10 in Scheme 2 may be reduced by standard means known in the art, such as reacting with 3 molar equivalents of tetrabutylammonium boronate and 4 molar equivalents of ethylbromide in a solvent mixture consisting of dichloromethane:THF:water (5:2:2). Work-up and purification by standard means affords product 11 which are compounds of the formula I in which $R_4$=OH (Examples 12 and 16). The alcohol products 11 can be reacted with 0.5 molar equivalents $PBr_3$ in an inert solvent such as dichloromethane at room temperature. The reacted mixture after work-up and purification yields the corresponding bromides 12 (Examples 13a and 17a). These alkyl bromides may be converted to compounds of formula I in which $R_4$=CN by reaction with sodium cyanide in a polar solvent or solvent mixture such as water:DMF (1:9) and heating at 50° C. The reacted mixture gives after work-up and chromatography the benzylcyanide products 13 (Example 13 and 17). In addition, the bromide intermediates 13 can be converted to compounds of formula I in which $R_4$=phosphonic acid diesters by reaction with trialkylphosphites under standard Arbusov reaction conditions. For example, the reaction of Example 13a with triethyl phosphite in large excess (10–12 molar equivalents versus bromide 12) in toluene at reflux for at least 2 days yields the corresponding dialkylphosphonate ester, compound 14 (Example 14) in Scheme 2. Simple hydrolysis of this product in aqueous acid solvent such as in hot hydrochloric acid gives the corresponding phosphonic acid 15 (Example 15) after work-up and purification.

Scheme 3 depicts a synthesis of compounds of formula I in which $R_4$=COOH and is connected to the aromatic ring by an intervening double bond (alkenyl carboxylic acid). A bromophenol of general structure 16 is coupled to iodonium salt 17 in the same manner as described above to give the diaryl ether product 18. Reaction of diaryl ether 18 with an acrylate ester such as ethyl acrylate, using palladium acetate, triphenyl phosphine and triethylamine in a solvent such as acetonitrile with heating at elevated temperatures gives a cinnamate ester product which, after removal of the ester and methyl ether as described previously, gives the product alkenyl carboxylic acid 19 (Example 18).

Scheme 3

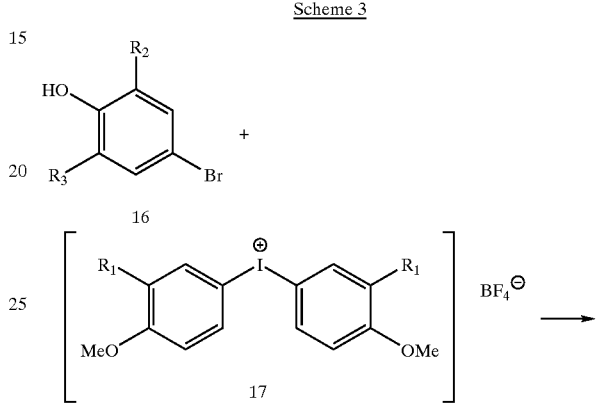

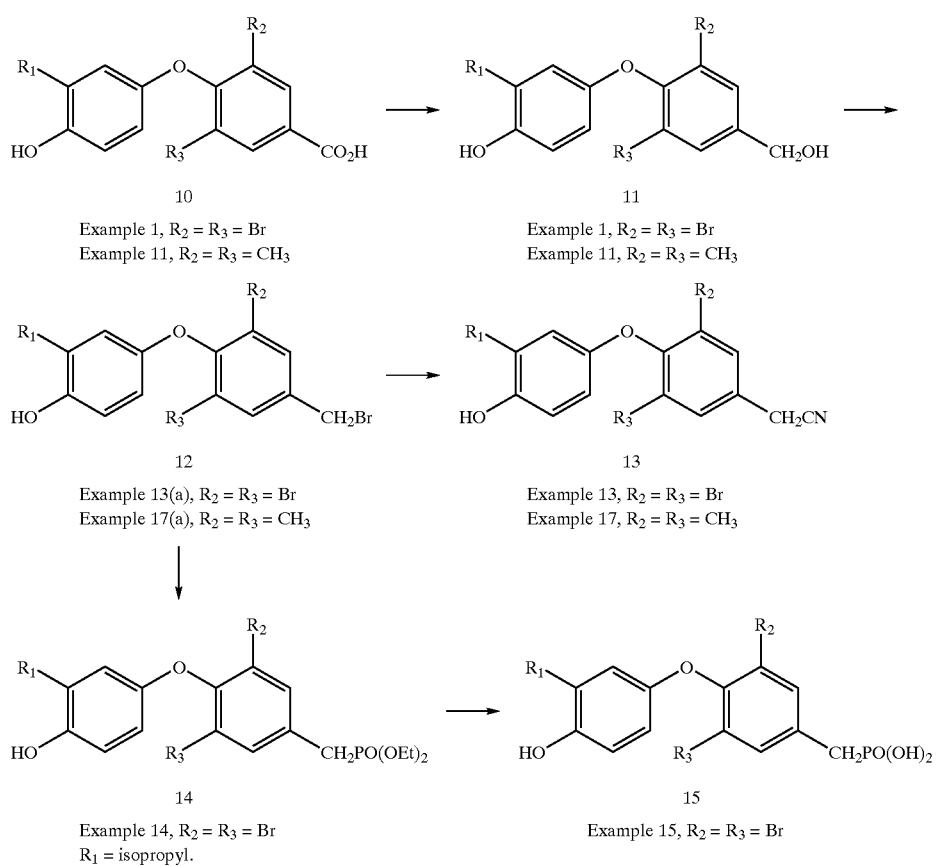

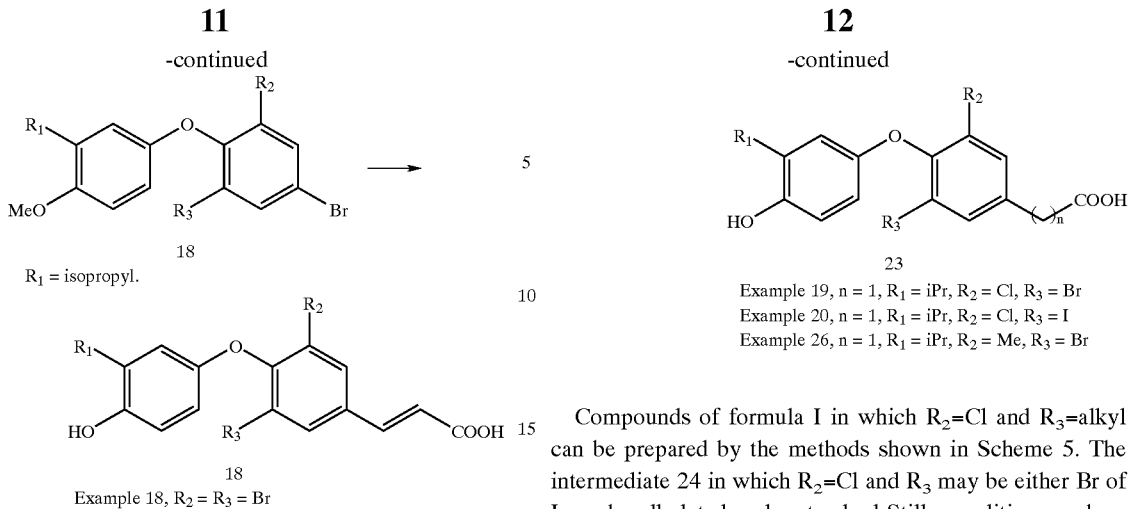

Examples of compounds of formula I in which $R_2$ is different from $R_3$ can be synthesized by the method shown in Scheme 4. Standard halogenation conditions are well-known to those versed in the art to convert the tri-substituted phenol ester intermediate 20 to product 21 in which $R_3$ is halogen and is different from $R_2$. For example, iodination can be achieved by using iodine in glacial acetic acid in the dark. Similarly, bromination can be accomplished by substituting bromine under the same reaction conditions. The product phenol 21 is then coupled to iodonium salt 2 to give the diaryl ether product 22. The ester group R and the methyl ether protecting groups are removed by procedures already described above to give the final product 23 where $R_3$ is halogen and is different from $R_2$ (Examples 19, 20 and 26).

Compounds of formula I in which $R_2$=Cl and $R_3$=alkyl can be prepared by the methods shown in Scheme 5. The intermediate 24 in which $R_2$=Cl and $R_3$ may be either Br of I can be alkylated under standard Stille conditions such as using tetramethyl tin [$(Me)_4Sn$] or tetraethyl tin [$(Et)_4Sn$] in the presence of tetrakis(triphenylphosphine)palladium in a solvent such as toluene. Heating this mixture in the dark under an inert atmosphere yields, after normal work-up and purification, the product 25 in which $R_2$=Cl and $R_3$=alkyl. Removal of the methyl ether and ester protecting groups under standard conditions well-known to those versed in the art yields the final product 26 (Examples 21 and 22).

The reduction product 27 (Example 23) was obtained under the reaction conditons described in Scheme 5.

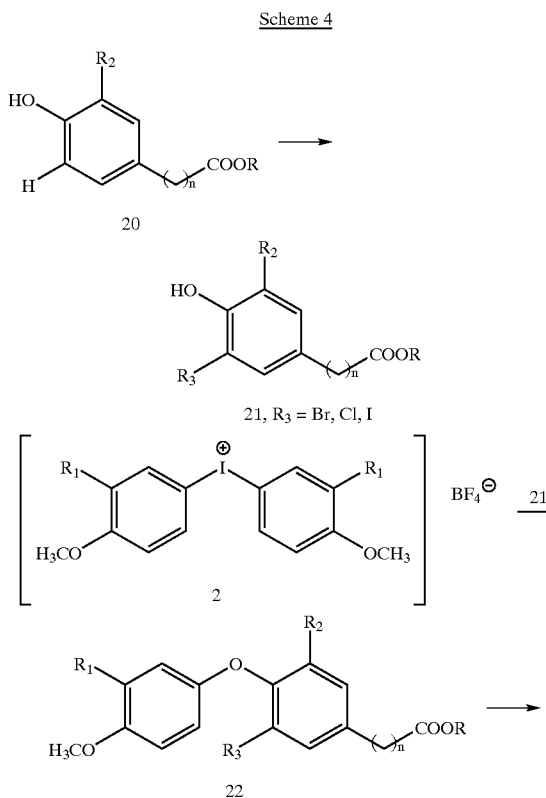

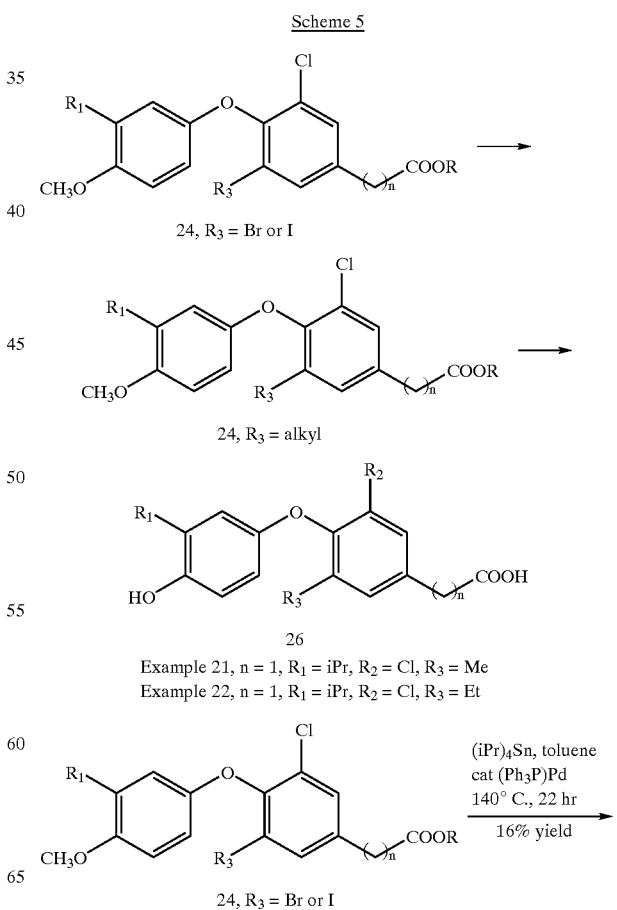

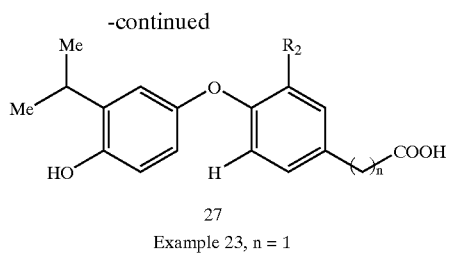

27

Example 23, n = 1

With respect to the above reaction schemes, although the various $R_1$, $R_2$, $R_3$, $R_4$ and n moieties are specifically defined, unless otherwise indicated, it is to be understood that $R_1$, $R_2$, $R_3$, and $R_4$ may be any of the groups encompassed thereby and n may be 0, 1, 2, 3 or 4.

The compounds of the invention are agonists, that are preferably selective for the thyroid hormone receptor-beta, and as such are useful in the treatment of obesity, hypercholesterolemia and atherosclerosis by lowering of serum LDL levels, alone or in combination with a cholesterol lowering drug such as an HMG CoA reductase inhibitor, amelioration of depression alone or in combination with an antidepressant, and stimulation of bone formation to treat osteoporosis in combination with any known bone resorption inhibitor such as alendronate sodium. In addition, the compounds of the invention may be useful as replacement therapy in elderly patients with hypothyroidism or subclinical hypothyroidism who are at risk for cardiovascular complications, and in the treatment of non-toxic goiter; in the management of papillary or follicular thyroid cancer (alone or with T4); in the treatment of skin disorders such as psoriasis, glaucoma, cardiovascular disease such as in the prevention or treatment of atherosclerosis, and congestive heart failure.

The compounds of the invention can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension or in other type carrier materials such as transdermal devices, iontophoretic devices, rectal suppositories, inhalant devices and the like. The composition or carrier will contain about 5 to about 500 mg per unit of dosage of a compound-of formula I. They may be compounded in conventional matter with a physiologically acceptable vehicle or carrier, excipient, binder, preservative, stabilizer, flavor, etc., as called for by accepted pharmaceutical practice.

The following working Examples represent preferred embodiments of the present invention.

EXAMPLE 1

3,5-Dibromo-4-(4-hydroxy-3-isopropylphenoxy) benzoic Acid (a) To a suspension of bis(3-isopropyl-4-methoxyphenyl)iodonium tetrafluoroborate (prepared by the method of Yokayama et al, Journal of Medicinal Chemistry 1995, 38, 695–707) (37 g) and copper bronze (6.1 g) in dichloromethane (150 ml), was added a solution of methyl 3,5-dibromo-4-hydroxybenzoate (15 g) and triethylamine (5.4 g) in dichloromethane (100 ml) dropwise at room temperature. The mixture was stirred overnight and then filtrated through Celite. After concentration, the resulting residue was passed through a short silica gel column eluted with ethyl acetate/light petroleum ether (5/95). The pure fractions were pooled and concentrated to dryness. The residue was recrystallized from methanol affording 19.5 g (89%) of methyl 3,5-dibromo -4-(4'-methoxy-3'-isopropylphenoxy)-benzoate.

(b) The above ester (6.5 g) was hydrolysed by treatment with 1 M aqueous NaOH (60 ml) and methanol (150 ml) to give 3,5-dibromo -4-(4'-methoxy-3'-isopropyl-phenoxy) benzoic acid (6.3 g, 99%).

(c) The above ester (2 g) was demethylated with boron tribromide (1M, 26 ml) in methylene chloride at 0° C. The mixture was stirred overnight at room temperature before quenching with a water/ice mixture. The layers were separated and the water layer extracted with methylene chloride. The combined organic extracts were dried, filtered and concentrated. The resulting residue was recrystallized to give 3,5-dibromo-4-(4-hydroxy-3-isopropylphenoxy) benzoic acid (1.85 g, 98%).

EXAMPLE 2

3,5-Dibromo-4-(4-hydroxy-3-isopropylphenoxy) benzyliodide a) Methyl 3,5-dibromo-4-(4-methoxy-3-isopropyl-phenoxy)-benzoate (Example 1a) (4.6 g) was treated with a 1 M solution of diisobutyl aluminium hydride(DIBAL) in THF (40 ml) at 0° C. and then warmed to room temperature and stirred for 1 hour. The reaction mixture was poured into an ice-cold 1 M HCl solution and extracted with ethyl acetate 3 times. The organic layer was washed (brine), dried, filtered and concentrated to dryness affording 3,5-dibromo-4-(4-methoxy-3-isopropylphenoxy)benzylalcohol (4.15 g, 96%) as oil which became a white solid after standing.

b) The above alcohol (215 mg) was added into a mixture of $P_2O_5$ (36 mg) and $H_3PO_4$ (490 mg) followed by addition of sodium iodide (150 mg). The mixture was stirred at 120° C. for 15 min and then partitioned between water and ethyl acetate. The organic layer was washed with $Na_2S_2O_3$ and brine, dried, filtered and concentrated. The residue was crystallized from petroleum ether to give 3,5-dibromo-4-(4-methoxy-3-isopropylphenoxy)-benzyliodide (170 mg, 63%).

c) The above iodide (300 mg) was demethylated with boron tribromide to give 3,5-dibromo-4-(4-hydroxy-3-isopropylphenoxy)benzyliodide (220 mg, 75%).

EXAMPLE 3

3,5-Dibromo-4-(4-hydroxy-3-isopropylphenoxy) phenylacetic Acid a) Bromine (35.2 g) was added dropwise to a suspension of methyl .4-hydroxy-phenylacetate (16.6 g) in $H_2O$ (500 ml). After 1 day stirring, the mixture was partitioned between $H_2O$ and ethyl acetate. The organic layer was washed with aqueous sodium thiosulfate, dried, filtered and concentrated. The residue was recrystallized from methanol to give 16 g of methyl 3,5-dibromo-4-hydroxy-phenylacetate as a light yellow solid (49%).

b) The above phenol (5 g) was coupled to bis(3-isopropyl-4-methoxyphenyl)iodonium tetrafluoroborate (9.5 g) as described in Example 1a. Purification by column chromatography and recrystallization from methanol gave 7.3 g (83%) of methyl 3,5-dibromo-4-(4-methoxy-3-Isopropyl-phenoxy)phenylacetate.

c) The above ester (2.4 g) was demethylated with boron tribromide as described in Example 2c The crude product was recrystallized from dichloromethane and light petroleum ether to give 1.37 g of 3,5-dibromo-4-(4'-hydroxy-3'-isopropylphenoxy)phenylacetic acid (62%).

EXAMPLE 4

3,5-Dibromo-4-(4-hydroxy-3-isopropylphenoxy) phenyl-propionic Acid (a) Methyl 4-hydroxy-phenylproprionate (9b) was brominated using the method described in Example 3a to give 15.8 g (93.5%) of methyl 3,5-dibromo-4-hydroxy-phenylpropionate a light yellow solid.

(b) The above phenol (3.4g) was coupled to bis(3-isopropyl-4-methoxyphenyl)iodonium tetrafluoroborate (7.7 g) using the method described in Example 1a to give 2.8 g (60%) of methyl 3,5-dibromo-4-(4-methoxy-3-isopropyl-phenoxy)phenylpropionate.

(c) The above ester (2.4 g) was demethylated with boron tribromide using the method described in Example 1c The crude product was recrystallized from dichloromethane and light petrolium ether to give 1.37 g (62%) of 3,5-dibromo-4-(4-hydroxy-3-isopropylphenoxy)phenylpropionic acid.

EXAMPLE 5

3,5-Dichloro-4-(4-hydroxy-3-isopropylphenoxy) benzoic Acid (a) Methyl 3,5-dichloro-4-hydroxybenzoate (10 g) was coupled with bis(3-isopropyl-4-methoxyphenyl)iodonium tetrafluoroborate (35 g) using the method described in Example 1a. Purification by column chromatography (silica gel, 95:5 light petroleum ether/ethylacetate) followed by recrystallization from methanol gave 8.42 g (51%) of methyl 3,5-dichloro-4-(4-methoxy-3-isopropylphenoxy)-benzoate.

(b) The above methoxy compound (100 mg) was demethylated and hydrolysed using the method described in Example 1c to give 65 mg (71%) of 3,5-dichloro-4-(4-hydroxy-3-isopropylphenoxy)benzoic acid.

EXAMPLE 6

3,5-Dichloro-4-(4-hydroxy-3-isopropylphenoxy) benzylalcohol a) Methyl 3,5-dichloro-4-(4-methoxy-3-isopropyl-phenoxy)benzoate (Example 5a) (3.0 g) was treated with a 1 M solution of diisobutyl aluminium hydride (DIBAL) in THF (32.5 ml) at 0° C. and then warmed to room temperature and stirred overnight. The reaction mixture was poured into an ice-cold 1 M HCl solution and extracted with ethyl acetate three times. The organic layer was washed (brine), dried, filtered and concentrated to dryness affording 3,5-dichloro-4-(4-methoxy-3-isopropylphenoxy)benzylalcohol (3.21 g, 100%) as an oil.

b) The above alcohol (200 mg) was demethylated using the method described in Example 1c to give 104 mg (59%) of 3,5 dichloro-4-(4-hydroxy-3-isopropyl-phenoxy) benzylalcohol.

EXAMPLE 7

3,5-Dichloro-4-(4-hydroxy-3-isopropylphenoxy) benzyliodide a) 3,5-Dichloro-4-(4-methoxy-3-isopropylphenoxy)-benzylalcohol (3.21 g) (Example 6a) was added into a mixture of $P_2O_5$ (576 mg) and $H_3PO_4$ (5.5 ml) followed by addition of sodium iodide (2.43 g). The mixture was stirred at 120° C. for 15 min and then partitioned between water and ethyl acetate. The organic layer was washed with an aqueous solution of $Na_2S_2O_3$ and brine, dried, filtered and concentrated. The residue was crystallized from petroleum ether to give 2.9 g (79%) of 3,5-dichloro-4-(4-methoxy-3-isopropylphenoxy)benzyliodide.

b) The above iodide (130 mg) was demethylation using the method described in Example 1c to give 76 mg (60%) of 3,5 dichloro-4-(4-hydroxy-3-isbpropylphenoxy)-benzyliodide.

EXAMPLE 8

3,5-Dichloro-4-(4-hydroxy-3-isopropylphenoxy) phenyl-propionic Acid a) Sodium (46 mg) in small pieces was added into a dry flask containing t-butanol. The mixture was refluxed for 1 hour or until the sodium was completely dissolved. Ethyl malonate (320 mg) was added and the reaction mixture was warmed at 90° C. for 1 hour followed by addition of the iodide (Example 7a, 451 mg) in portions. The mixture was stirred under reflux for three hours and concentrated. The residue was stirred under reflux with potassium hydroxide and water (1:1) overnight. The resulting residue was partitioned between ethyl acetate and concentrated Hcl. The organic layer was dried, filtered and concentrated to give a white solid which was transferred into a small flask which was heated at 180° C. for three hours. The resulting residue was chromatographed on silica gel and eluted with methanol/chloroform (1/9). The pure fractions were pooled and concentrated affording 3,5-Dichloro-4-(4-methoxy-3-isopropylphenoxy)phenylpropionic acid (152 mg, 20%).

b) The above acid (116 mg) was demethylated with boron trifluoride dimethylsulfide complex to give 3,5-dichloro-4-(4-hydroxy-3-isopropylphenoxy)phenylpropionic acid (33 mg, 30%).

EXAMPLE 9

3, 5-Dichloro-4-(4-hydroxy-3-isopropylphenoxy) phenyl-acetonitrile a) To a solution of sodium cyanide (400 mg) in water (1 ml), the above iodide (Example 7a, 900 mg) in absolute ethanol (3 ml) was added. The reaction mixture became homogeneous after heating and was stirred under reflux for 2 hours. The reaction mixture was poured into crushed ice and partitioned between water and ethyl acetate. The organic layer was dried, filtered and concentrated and the residue was chromatographed on silica gel and eluted with ethyl acetate/petroleum ether (1/8). The pure fractions were pooled and concentrated to give 3,5-dichloro-4-(4-methoxy-3-isopropylphenoxy)phenyl-acetonitrile (440 mg, 63%).

b) The above methoxynitrile (170 mg) was demethylated using the method described in Example 1c to give 3,5-dichloro-4-.(4-hydroxy-3-isopropylphenoxy)-phenylacetonitrile (147 mg, 90%).

EXAMPLE 10

3,5-Dichloro-4-(4-hydroxy-3-isopropylphenoxy) phenylacetic Acid

To a solution of nitrile 9b (760 mg) dissolved in acetic acid (10 ml) was added dropwise a mixture of concentrated sulfuric acid (10 ml) and water (10 ml) was added dropwise.

The reaction mixture was heated at 105° C. for 3 hours and partitioned between ice-cold water and ethyl acetate. The organic layer was dried, filtered and concentrated to give 3,5-dichloro-4-(4-hydroxy-3-isopropylphenoxy) phenylacetic acid (638 mg, 77%).

EXAMPLE 11

3,5-Dimethyl-4-(4-hydroxy-3-isopropylphenoxy) benzoic Acid (a) Methyl 3,5-dimethyl-4-hydroxybenzoate (5.2 g) was coupled with bis(3-isopropyl-4-methoxyphenyl)iodonium tetrafluoroborate (22.1 g) using the method described in Example 1(a). Purification by column chromatography (silica gel, 97:3 light petroleum ether/ethylacetate) gave 8.3 g (87%) of methyl 3,5-dichloro-4-(4-methoxy-3-isopropylphenoxy)benzoate.

(b) The above methoxy compound (5 g) was demethylated and hydrolysed using the method described in Example 1(c). The residue was subjected to column chromatography (silica gel, 98:2:0.3 chloroform/methanol/acetic acid) to give 1.22 g (27%) of the title compound.

EXAMPLE 12

3,5-Dibromo -4-(4-hydroxy-3-isopropylphenoxy) benzylalcohol

A mixture of 3,5-dibromo-4-(4-hydroxy-3-isopropylphenoxy)benzoic acid (Example 1(c) (1.0 g, 3.3 mmol), tetrabutylammonium boronate (2.6 g, 9.9 mmol) and ethylbromide (1.0 ml, 13.2 mmol) in 25 ml of $CH_2Cl_2$ and 10 ml of tetrahydrofuran was stirred at room temperature over night. The reaction mixture was treated with 1M HCl and extracted several times with EtOAc. The combined organic phases were washed once with water followed by a saturated solution of NaCl. After drying over MgSO4, filtration and evaporation, the residue was purified by column chromathography (silica gel, 7:3 p-ether/EtOAc). This gave 0.922 g (98%) of 3,5-dibromo-4-(4-hydroxy-3-isopropylphenoxy) benzyl-alcohol.

EXAMPLE 13

3,5-Dibromo-4-(4-hydroxy-3-isopropylphenoxy) benzylcyanide (a) A solution of $PBr_3$ (125 mg, 0.463 mmol) in 5 ml of $CH_2Cl_2$ was added dropwise, under nitrogen, to a stirred solution of 3,5-dibromo-4-(4-hydroxy-3-isopropylphenoxy)-benzylalcohol (Example 12) (385 mg, 0.925 mmol) in 20 ml $CH_2Cl_2$ at 0° C. The reaction mixture was left to stand at room temperature over night and then diluted with $CH_2Cl_2$. The organic phase was washed with water, dried over MgSO4 and concentrated. The residue was purified by column chromatography (silica gel, 75:25 petroleum-ether/EtOAc) to give 160 mg (36%) of 3,5-dibromo-4-(4-hydroxy-3-isopropylphenoxy) benzylbromide.

(b) To a stirred solution the above bromide (135 mg, 0.282 mmol) in 0.85 ml of DMF and 0.09 ml of water at 50° C., NaCN (17 mg, 0.352 mmol) was added. After 30 minutes the reaction mixture was concentrated, treated with water and extracted twice with EtOAc. The combined organic phases were dried over $MgSO_4$, filtered and concentrated. The residue was purified by column chromathography (silica gel, 8:2 petroleum-ether/EtOAc) to give 80 mg (67%) of 3,5-dibromo-4-(4-hydroxy-3-isopropylphenoxy)-benzylcyanide.

EXAMPLE 14

3,5-Dibromo-4-(4-hydroxy-3-isopropylphenoxy) benzyl-phosphonic Acid, Diethyl Ester A mixture of 3,5-dibromo-4-(4-hydroxy-3-isopropylphenoxy)benzylbromide (Example 13a) (491 mg, 1.03 mmol), triethyl phosphite (3.98 g, 12 mmol) in 20 ml of toluene was refluxed for 48 hours. The reaction mixture was concentrated and the residue was precipitated with a mixture of petroleum ether and EtOAc (8:2) to give 308 mg (0.577 mmol, 56%) of 3,5-dibromo-4-(4-hydroxy-3-isopropylphenoxy)benzyl phosphonic acid, diethyl ester as a white solid.

EXAMPLE 15

3,5-Dibromo -4-(4-hydroxy-3-isopropylphenoxy) benzyl-phosphonic Acid

A mixture of 3,5-dibromo-4-(4-hydroxy-3-isopropylphenoxy) benzyl phosphonic acid, diethyl ester (21 mg, 0.0392 mmol) in 2 ml of 6 M HCl was refluxed for 24 hours. The reaction mixture was concentrated and the residue was recrystallized with EtOH/water to give 10 mg (0.021 mmol, 53%) of 3,5-dibromo-4-(4-hydroxy-3-isopropylphenoxy)-benzylphosphonic acid as white crystalls.

EXAMPLE 16

3,5-Dimethyl-4-(4-hydroxy-3-isopropylphenoxy) benzylalcohol

A mixture consisting of the above acid (Example 11b, 1.0 g), tetrabutylammonium boronate (2.6 g, 9.9 mmol) and ethylbromide (1.0 ml, 13.2 mmol) in 25 ml of $CH_21C_2$ and 10 ml of tetrahydrofuran was stirred at room temperature over night. The reaction mixture was treated with 1M HCl and extracted several times with EtOAc. The combined organic phases were washed once with water followed by a saturated solution of NaCl. After drying over MgSO4, filtration and evaporation, the residue was purified by column chromathography (silica gel, 7:3 p-ether/EtOAc). This gave 0.922 g (98%) of the title compound.

EXAMPLE 17

3,5-Dimethyl-4-(4-hydroxy-3-isopropylphenoxy) phenyl-acetonitrile (a) A solution of PBr3 (401 mg, 1.48 mmol) in 10 ml of $CH_2Cl_2$ was added dropwise, under nitrogen, to a stirred solution of the above alcohol (Example 16, 850 mg) in 20 ml CH2C12 at 0° C. The reaction mixture was left to stand at room temperature over night and then diluted with $CH_2Cl_2$. The organic phase was washed with water, dried over $MgSO_4$ and concentrated. The residue was purified by column chromatography (silica gel, 9:1 petroleum-ether/ EtOAc) to give 465 mg of 3,5-dimethyl-4-(4-hydroxy-3-isopropyl-phenoxy)benzylbromide b) To a stirred refluxed solution of the above nitrile (325 mg) in 2.0 ml of DMF and 0.2 ml of water, NaCN (42 mg) was added. After 2 hours the reaction mixture was concentrated, treated with water and extracted twice with EtOAc. The combined organic phases were dried over $MgSO_4$, filtered and concentrated. The residue was purified by column chromatography (silica gel, 8:2 petroleum-ether/EtOAc) to give 171 mg (85%) of the title compound.

EXAMPLE 18

3,5-Dibromo-4-(4-hydroxy-3-isopropylphenoxy) cinnamic Acid (a) 2,4,6-Tribromo-phenol (3.15 g) was coupled to bis (3-isopropyl-4-methoxyphenyl) iodoniumn tetraf luoroborate (7.7 g) using the method described in Example 1(a). Purification by column chromatography and recrystallization from methanol gave 4.5 g (94%) of methyl 1,3,5-tribromo-4-(4-methoxy-3-isopropylphenoxy) benzene.

b) A mixture of above tri-bromobenzene, (2.9 g) ethyl acrylate (0.9), palladium acetate (23 mg), triethyla-rine (0.6 g), triphenylphosphine (30 mg) in acetonitrile was stirred at 120° C. for 5 days. Purification by column chromatography and recrystallization from methanol gave 300mg (12%) of ethyl 3,5-dibromo -4-(4-methoxy-3-isopropylphenoxy) cinnamate.

c) The above ester (2.4 g) was demethylated with boron tri-bromide using the method described in Example 2(c). The crude product was recrystallized from dichloromethane and light petrolium ether to give 1.37 g of 3,5-dibromo-4-(4-hydroxy-3-isopropylphenoxy) cinnamic Acid (62%).KB 131 109.

EXAMPLE 19

3-Bromo-5-chloro-4-(4-hydroxy-3-isopropylphenoxy)-phenylacetic Acid a) To a solution of 3-chloro-4-hydroxyphenylacetic acid (2.5 g) in glacial acetic acid (35 mL) was added 0.8 mL of neat bromine carefully while stirring. The mixture was stirred in dark at ambient temperature for 51 h. The resulting mixture was diluted with water, extracted with ethyl acetate, dried and concentrated in vacuo to afford 3-bromo-5-chloro-4-hydrox-yphenylacetic acid. This crude product was dissolved in methanol (15 mL), treated with concentrated sulfuric acid (1 mL) carefully, stirred at reflux for 18 h. Cooled reaction mixture was concentrated under reduced pressure, diluted with water carefully, extracted with dichloromethane. The combined organic layers were dried and concentrated. Flash column chromatography on silica gel with ethyl acetate/hexane (0–50% gradient elution) afforded 3-bromo-5-chloro-4-hydroxyphenylacetic acid methyl ester (2.5 g, 68%).

b) 3-Bromo-5-chloro-4-hydroxyphenylacetic acid methyl ester (1.1 g) was coupled with bis (3-isopropyl-4-methoxyphenyl)iodonium tetrafluoroborate (2.9 g) by the procedure described in Example 1(a) to afford 3-bromo-5-chloro-4-(4-methoxy-3-isopropylphenoxy) phenylacetic acid methyl ester (1.1 g, 67%).

c) A solution of the above product (32 mg) in dichloromethane (2 mL) was treated with boron tribromide (1 M, 1 mL) under nitrogen and stirred at ambient temperature for two days. The reaction mixture was poured to stirring water and extracted with ethyl acetate from 1 N HCl. The combined organic layers were dried and concentrated. The desired 3-bromo-5-chloro-4-(4-hydroxy-3-isopropylphenoxy)-phenylacetic acid was purified using reverse-phase preparative HPLC eluting with methanol/water (30–90%) (15 mg, 50%).

EXAMPLE 20

3-chloro-5-iodo-4-(4-hydroxy-3-isopropylphenoxy)-phenylacetic Acid a) To a solution of 3-chloro-4-hydroxyphenylacetic acid (1.25 g) in glacial acetic acid (20 mL) was added 2.0 g of iodine crystals while stirring. The mixture was stirred in dark at ambient temperature for 2 days. The resulting mixture was diluted with water, extracted with ethyl acetate, dried and concentrated in vacuo to afford 3-chloro-5-iodo-4-hydroxyphenylacetic acid. This crude product was dissolved in methanol (30 mL), treated with concentrated sulfuric acid (2 mL) carefully, stirred at reflux for 20 h. Cooled reaction mixture was concentrated under reduced pressure, diluted with water, extracted with dichloromethane. The combined organic layers were dried and concentrated. Flash column chromatography on silica gel with ethyl acetate/hexane (0–50% gradient elution) afforded 3-chloro-5-iodo-4-hydroxyphenylacetic acid methyl ester (90 mg, 4%).

b) 3-Chloro-5-iodo-4-hydroxyphenylacetic acid methyl ester (90 mg) was coupled with bis (3-isopropyl-4-methoxyphenyl)iodonium tetrafluoroborate (310 mg) by the procedure described in Example 1(a) to afford 3-chloro-5-iodo-4-(4-methoxy-3-isopropylphenoxy) phenylacetic acid methyl ester (70 mg, 54%).

c) A solution of the above product (30 mg) in dichloromethane (2 mL) was treated with boron tribromide (1 M, 1 mL) under nitrogen and stirred at ambient temperature for 22 h. The reaction mixture was poured to stirring water and extracted with ethyl acetate from 1 N HCl. The combined organic layers were dried and concentrated. The desired 3-chloro-5-iodo-4-(4-hydroxy-3-isopropylphenoxy)-phenylacetic acid was purified using reverse-phase preparative HPLC eluting with methanol/water (30–90%) (18 mg, 64%).

EXAMPLE 21

3-Chloro-5-methyl-4-(4-hydroxy-3-isopropylphenoxy)-phenylacetic Acid a) A solution of 3-bromo-5-chloro-4-(4-methoxy-3-isopropylphenoxy) phenylacetic acid methyl ester (50 mg) in toluene (2 mL) in a pressure tube was degassed with nitrogen, treated with tetrakis(triphenylphosphine)-palladium (47 mg) and tetramethyltin (0.3 mL) sequentially at ambient temperature. The pressure tube was then sealed and wrapped with aluminum foil. The reaction mixture was stirred at 140° C. in dark for 22 h. Cooled reaction mixture was chromatographied on silica gel with ethyl acetate/hexane (0–25% gradient elution) afforded 3-chloro-5-methyl-4-(4-hydroxy-3-isopropylphenoxy)phenylacetic acid methyl ester (36 mg, 85%).

b) A solution of the above product (36 mg) in dichloromethane (2 mL) was treated with boron tribromide (1 M, 1 mL) under nitrogen and stirred at ambient temperature for 29 h. The reaction mixture was poured to stirring water and extracted with ethyl acetate from 1 N HCl. The combined organic layers were dried and concentrated. The desired 3-chloro-5-methyl-4-(4-hydroxy-3-isopropylphenoxy)-phenylacetic acid was purified using reverse-phase preparative HPLC eluting with methanol/water (30–90%) (16 mg, 48%).

EXAMPLE 22

3-Chloro-5-ethyl-4-(4-hydroxy-3-isopropylphenoxy)-phenylacetic Acid a) A solution of 3-bromo-5-chloro-4-(4-methoxy-3-isopropylphenoxy) phenylacetic acid methyl ester (50 mg) in toluene (2 mL) in a pressure tube was degassed with nitrogen, treated with tetrakis(triphenylphosphine)-palladium (25 mg) and tetraethyltin (0.3 mL) sequentially at ambient temperature. The pressure tube was then sealed and wrapped with aluminum foil. The reaction mixture was stirred at 140° C. in dark for 17 h. Cooled reaction mixture was chromatographied on silica gel with ethyl acetate/ hexane (0–25% gradient elution) afforded 3-chloro-5-ethyl-4-(4-hydroxy-3-isopropylphenoxy)phenylacetic acid methyl ester (40 mg, 90%).

b) A solution of the above product (40 mg) in dichloromethane (2 mL) was treated with boron tribromide (1 M, 1 mL) under nitrogen and stirred at ambient temperature for 20 h. The reaction mixture was poured to stirring water and extracted with ethyl acetate from 1 N HCl. The combined organic layers were dried and concentrated. The desired 3-chloro-5-ethyl-4-(4-hydroxy-3-isopropyl-phenoxy) phenylacetic acid was purified using reverse-phase preparative HPLC eluting with methanol/water (30–90%) (5 mg, 13%).

EXAMPLE 23

3-Chloro-4-(4-hydroxy-3-isopropylphenoxy) phenylacetic Acid

A solution of 3-bromo-5-chloro-4-(4-methoxy-3-isopropylphenoxy) phenylacetic acid methyl ester (100 mg) in toluene (2 mL) in a pressure tube was degassed with nitrogen, treated with tetrakis(triphenylphosphine)-palladium (54 mg) and tetraisopropyltin (0.5 mL) sequentially at ambient temperature. The pressure tube was then sealed and wrapped with aluminum foil. The reaction mixture was stirred at 140° C. in dark for 22 h. Cooled reaction mixture was chromatographied on silica gel with ethyl acetate/hexane (0–25% gradient elution) afforded 3-chloro-4-(4-hydroxy-3-isopropylphenoxy)phenylacetic acid methyl ester. A solution of this product in dichloromethane (2 mL) was treated with boron tribromide (1 M, 1 mL) under nitrogen and stirred at ambient temperature for 3 h. The reaction mixture was poured to stirring water and extracted with ethyl acetate from 1 N HCl. The combined organic layers were dried and concentrated. The residue was dissolved in THF:MeOH:H2O (3:1:1, 2 mL), treated with LiOH (20 mg) in one portion and stirred at ambient temperature for 19 h. The reaction mixture was extracted with ethyl acetate from 1 N HCl, dried, and concentrated. 3-chloro-4-(4-hydroxy-3-isopropylphenoxy)-phenylacetic acid was purified using reverse-phase preparative HPLC eluting with methanol/water (30–90%) (12 mg, 16%).

EXAMPLE 24

3,5-dimethyl-4-(4-hydroxy-3-isopropylphenoxy) phenylacetic Acid

A solution of 3,5-dibromo-4-(4-methoxy-3-isopropylphenoxy) phenylacetic acid (25 mg) in dimethylformaldehyde (1 mL) in a pressure tube was degassed with nitrogen, treated with tetrakis(triphenylphosphine)-palladium (12 mg) and tetramethyltin (0.3 mL) sequentially at ambient temperature. The pressure tube was then sealed and wrapped with aluminum foil. The reaction mixture was stirred at 140° C. in dark for 23 h. Cooled reaction mixture was filtered through celite, rinsed with ethyl acetate. The filtrate was extracted with ethyl acetate from 1 N HCl, dried, and concentrated. Reverse-phase preparative HPLC eluting with methanol/water (30–90%) afforded 3,5-dimethyl-4-(4-hydroxy-3-isopropylphenoxy)phenylacetic acid (9 mg, 50%).

EXAMPLE 25

3-Ethyl-5-methyl-4-(4-hydroxy-3-isopropylphenoxy)-phenylacetic Acid

A solution of 3,5-dibromo-4-(4-methoxy-3-isopropylphenoxy) phenylacetic acid methyl ester (37 mg) in toluene (2 mL) in a pressure tube was degassed with nitrogen, treated with tetrakis(triphenylphosphinepalladium (17 mg), tetraethyltin (0.1 mL) and tetramethyltin (0.1 mL) sequentially at ambient temperature. The pressure tube was then sealed and wrapped with aluminum foil. The reaction mixture was stirred at 140° C. in dark for 22 h. Cooled reaction mixture was chromatographied on silica gel with ethyl acetate/hexane (0–25% gradient elution) afforded a mixture of products. A solution of these products in dichloromethane (2 mL) was treated with boron tribromide (1 M, 1 mL) under nitrogen and stirred at ambient temperature for 24 h. The reaction mixture was poured to stirring water and extracted with ethyl acetate from 1 N HCl. The combined organic layers were dried and concentrated. The desired 3-ethyl-5-methyl-4-(4-hydroxy-3-isopropylphenoxy) phenylacetic acid was purified using reverse-phase preparative HPLC eluting with methanol/water (30–90%) (4 mg, 15%).

EXAMPLE 26

3-Bromo-5-methyl-4-(4-hydroxy-3-isopropylphenoxy)-phenylacetic Acid a) To a solution of 4-methoxy-3-methylphenylacetic acid (0.43 g) in glacial acetic acid (7 mL) was added 0.2 mL of neat bromine carefully while stirring. The mixture was stirred in dark at ambient temperature for 27 h. The resulting mixture was diluted with brine, extracted with ethyl acetate, dried and concentrated in vacuo to afford 3-bromo-5-methyl-4-methoxyphenylacetic acid. This crude product was dissolved in methanol (30 mL), treated with concentrated sulfuric acid (1 mL) carefully, stirred at reflux for 16 h. Cooled reaction mixture was concentrated under reduced pressure, diluted with brine, extracted with ethyl acetate. The combined organic layers were dried and concentrated in vacuo. The residue was dissolved in dichloromethane (10 mL), treated with boron tribromide (1 M, 2 mL) under nitrogen and stirred at ambient temperature for 1 h. The reaction mixture was poured to stirring water and extracted with ethyl acetate from 1 N HCl. The combined organic layers were dried and concentrated. Flash column chromatography on silica gel with ethyl acetate/hexane (0–50% gradient elution) afforded 3-bromo-5-methyl-4-hydroxyphenylacetic acid methyl ester (0.21 g, 34%).

b) 3-Bromo-5-methyl-4-hydroxyphenylacetic acid methyl ester (0.2 g) was coupled with bis (3-isopropyl-4-methoxyphenyl)iodonium tetrafluoroborate (0.7 g) by the procedure described in Example 1(a) to afford 3-bromo-5-methyl-4-(4-methoxy-3-isopropylphenoxy) phenylacetic acid methyl ester (0.15 g, 48%).

c) A solution of the above product (84 mg) in dichloromethane (3 mL) was treated with boron tribromide (1 M, 2 mL) under nitrogen and stirred at ambient temperature for 4 h. The reaction mixture was poured to stirring water and extracted with ethyl acetate from 1 N HCl. The combined organic layers were dried and concentrated. The desired 3-bromo-5-methyl-4-(4-hydroxy-3-isopropylphenoxy)-phenylacetic acid was purified using reverse-phase preparative HPLC eluting with methanol/water (30–90%) (25 mg, 32%).

What is claimed is:
1. A compound having the formula

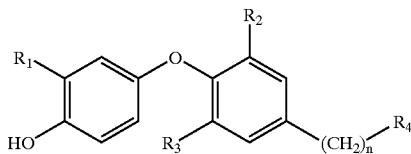

wherein
- $R_1$ is alkyl of 1 to 4 carbons or cycloalkyl of 3 to 7 carbons;
- $R_2$ and $R_3$ are the same or different and are hydrogen, fluorine, chlorine, bromine, alkyl of 1 to 3 carbons or cycloalkyl of 3 to 5 carbons, at least one of $R_2$ and $R_3$ being other than hydrogen;
- n is an integer from 0 to 4;
- $R_4$ is an aliphatic hydrocarbon, an aromatic hydrocarbon, hydroxy, halogen, cyano, —P(OH)$_2$ group or ester thereof, an alkenyl carboxylic acid or ester thereof, or a pharmaceutically acceptable salt thereof, and all stereoisomers thereof; or, provided that when n is 0 or 1, then $R_4$ is a COOH group or ester thereof, or a pharmaceutically acceptable salt thereof, and all stereoisomers thereof.

2. The compound as defined in claim 1 wherein n is 0 or 1 or 2.

3. The compound as defined in claim 1 wherein $R_2$ and $R_3$ are each independently fluorine, chlorine, or bromine.

4. The compound as defined in claim 1 wherein $R_2$ and $R_3$ are each independently an alkyl group.

5. The compound as defined in claim 1 wherein one of $R_2$ and $R_3$ is fluorine, chlorine, or bromine and the other is an alkyl group.

6. The compound as defined in claim 1 wherein one of $R_2$ and $R_3$ is fluorine, chlorine, or bromine and the other is hydrogen.

7. The compound as defined in claim 1 wherein one of $R_2$ and $R_3$ is alkyl and the other is hydrogen.

8. The compound as defined in claim 1 wherein $R_2$ and $R_3$ are independently Cl, Br, methyl or ethyl.

9. The compound as defined in claim 1 wherein $R_1$ is isopropyl.

10. The compound as defined in claim 1 wherein $R_4$ is carboxyl, halogen, hydroxy, cyano, an alkenoic acid residue, or a phosphonic acid.

11. The compound as defined in claim 1 which is
3,5-dibromo-4-(4-hydroxy-3-isopropylphenoxy)benzoic acid,
3,5-dibromo -4-(4-hydroxy-3-isopropylphenoxy)-benzyliodide,
3,5-dibromo -4-(4-hydroxy-3-isopropylphenoxy)-phenylacetic acid,
3,5-dibromo -4-(4-hydroxy-3-isopropylphenoxy)-phenylpropionic acid,
3, 5-dichloro-4-(4-hydroxy-3-isopropylphenoxy)benzoic acid,
3,5-dichloro-4-(4-hydroxy-3-isopropylphenoxy)-benzylalcohol,
3,5-dichloro-4-(4-hydroxy-3-isopropylphenoxy)-benzyliodide,
3,5-dichloro-4-(4-hydroxy-3-isopropylphenoxy)-phenylpropionic acid,
3,5-dichloro-4-(4-hydroxy-3-isopropylphenoxy)-phenylacetonitrile,
3,5-dichloro-4-(4-hydroxy-3-isopropylphenoxy)-phenylacetic acid,
3,5-dimethyl-4-(4-hydroxy-3-isopropylphenoxy)benzoic acid,
3,5-dibromo-4-(4-hydroxy-3-isopropylphenoxy)-benzylalcohol,
3,5-dibromo-4-(4-hydroxy-3-isopropylphenoxy)-benzylcyanide
3,5-dibromo-4-(4-hydroxy-3-isopropylphenoxy)-benzyl phosphonic acid, diethyl ester,
3,5-dibromo-4-(4-hydroxy-3-isopropylphenoxy)-benzylphosphonic acid,
3,5-dimethyl-4-(4-hydroxy-3-isopropylphenoxy)-benzylalcohol,
3,5-dimethyl-4-(4-hydroxy-3-isopropylphenoxy)-phenylacetonitrile,
3,5-dibromo -4-(4-hydroxy-3-isopropylphenoxy)-cinnamic acid,
3-bromo-5-chloro-4-(4-hydroxy-3-isopropylphenoxy)-phenylacetic acid,
3-chloro-5-iodo-4-(4-hydroxy-3-isopropylphenoxy)-phenylacetic acid,
3-chloro-5-methyl-4-(4-hydroxy-3-isopropylphenoxy)-phenylacetic acid,
3-chloro-5-ethyl-4-(4-hydroxy-3-isopropylphenoxy)-phenylacetic acid,
3-chloro-4-(4-hydroxy-3-isopropylphenoxy)-phenylacetic acid,
3,5-dimethyl-4-(4-hydroxy-3-isopropylphenoxy)-phenylacetic acid,
3-ethyl-5-methyl-4-(4-hydroxy-3-isopropylphenoxy)-phenylacetic acid,
3-bromo-5-methyl-4-(4-hydroxy-3-isopropylphenoxy)-phenylacetic acid,
or a pharmaceutically acceptable salt thereof.

12. The compound as defined in claim 1 having the structure

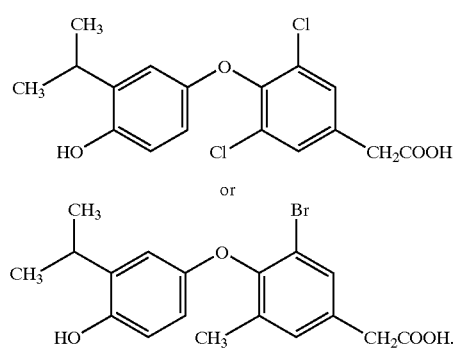

13. A method for preventing, inhibiting or treating a disease associated with metabolism dysfunction, or which is dependent on the expression of a T3 regulated gene, which comprises administering to a patient in need of treatment a therapeutically effective amount of a compound as defined in claim 1.

14. The method as defined in claim 13 wherein the disease associated with metabolism dysfunction or which is dependent on the expression of a T3 regulated gene is obesity, hypercholesterolemia, atherosclerosis, depression, osteoporosis, hypothyroidism, goiter, thyroid cancer, glaucoma, cardiac arrhythmia, or congestive heart failure.

15. A thyroid receptor ligand according to the following formula

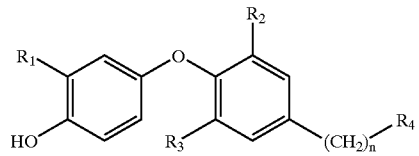

in which $R_2$ and $R_3$ are the same or different and are hydrogen, fluorine, chlorine, or bromine, or alkyl of 1 to 3 carbons, n is an integer between 0 and 4 and $R_4$ is selected from aliphatic and aromatic hydrocarbons, hydroxy, halogen, cyano, —$P(OH)_2$ group or ester thereof, or an alkenyl carboxylic acid or ester thereof, or a pharmaceutically acceptable salt thereof, and all stereoisomers thereof; or, provided that when n is 0 or 1, then $R_4$ is a COOH group or ester thereof, or a pharmaceutically acceptable salt thereof, and all stereoisomers thereof.

16. The thyroid receptor ligand according to claim 15, in which $R_2$ and $R_3$ are the same or different and are chlorine, bromine or methyl.

17. A method of producing a thyroid receptor ligand according to claim 15 which comprises reacting a compound of Formula II below with a compound of Formula III below, and demethylating the reaction product, to produce the ligand

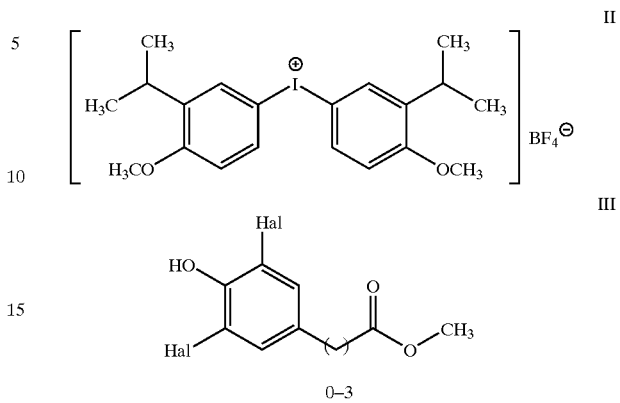

where Hal is halogen.

18. A pharmaceutical composition comprising an effective amount of a compound according to claim 1 or a pharmaceutically effective salt therefore, together with a pharmaceutically acceptable carrier.

19. A method of treatment of a patient with a T3 regulated gene disorder or disease, which comprises administering to a patient in need of treatment a therapeutically effective amount of a compound according to claim 1.

20. The method according to claim 19 in which the disorder or obesity is selected from hypothyroidism, hypercholesterolemia, obesity, skin disorders, glaucoma, cardiovascular disease, congestive heart failure, and other endocrine disorders related to thyroid hormone.

* * * * *